United States Patent
Schwartz et al.

(10) Patent No.: US 9,435,687 B1
(45) Date of Patent: Sep. 6, 2016

(54) METHOD TO REMOVE THE SPECTRAL COMPONENTS OF ILLUMINATION ENERGY FROM A SAMPLE SPECTRUM WITHOUT THE USE OF OPTICAL BARRIER FILTERS, AND APPARATUS FOR THE SAME

(71) Applicants: Abraham Schwartz, San Juan, PR (US); Martin C. Cohen, Laurel, MD (US); Peter Ingram, Raleigh, NC (US)

(72) Inventors: Abraham Schwartz, San Juan, PR (US); Martin C. Cohen, Laurel, MD (US); Peter Ingram, Raleigh, NC (US)

(73) Assignee: CENTER FOR QUANTITATIVE CYTOMETRY, San Juan, PR (US)

( * ) Notice: Subject to any disclaimer, the term of this patent is extended or adjusted under 35 U.S.C. 154(b) by 107 days.

(21) Appl. No.: 14/506,704

(22) Filed: Oct. 6, 2014

Related U.S. Application Data

(60) Provisional application No. 61/973,958, filed on Apr. 2, 2014.

(51) Int. Cl.
| | |
|---|---|
| *G01J 3/02* | (2006.01) |
| *G01J 3/18* | (2006.01) |
| *G01J 3/44* | (2006.01) |
| *G01N 21/27* | (2006.01) |

(52) U.S. Cl.
CPC ............... *G01J 3/0297* (2013.01); *G01J 3/18* (2013.01); *G01J 3/4406* (2013.01); *G01N 21/274* (2013.01)

(58) Field of Classification Search
CPC .. G01J 3/0297; G01J 1/0295; G01N 21/274; G01N 21/276; G01N 21/278
See application file for complete search history.

(56) References Cited

U.S. PATENT DOCUMENTS

| | | | | |
|---|---|---|---|---|
| 5,194,913 | A  * | 3/1993 | Myrick | G01N 21/65 |
| | | | | 250/458.1 |
| 6,281,971 | B1 * | 8/2001 | Allen | G01J 3/02 |
| | | | | 356/301 |
| 8,310,671 | B1 * | 11/2012 | Nguyen | G01J 3/44 |
| | | | | 356/301 |
| 9,182,280 | B1 * | 11/2015 | Gardner | G01J 3/0297 |
| 2008/0128622 | A1 * | 6/2008 | Weidmann | G01J 3/02 |
| | | | | 250/343 |
| 2011/0108720 | A1 * | 5/2011 | Ford | E21B 49/08 |
| | | | | 250/262 |
| 2011/0313635 | A1 * | 12/2011 | Blanc | F02D 41/1451 |
| | | | | 701/102 |
| 2015/0025847 | A1 * | 1/2015 | Baudelet | G01J 3/28 |
| | | | | 702/182 |
| 2015/0144791 | A1 * | 5/2015 | Simpkin | G01N 21/274 |
| | | | | 250/339.07 |
| 2015/0148627 | A1 * | 5/2015 | Baets | G01N 21/03 |
| | | | | 600/316 |

* cited by examiner

*Primary Examiner* — Kara E Geisel
*Assistant Examiner* — Shawn Decenzo
(74) *Attorney, Agent, or Firm* — Hoglund & Pamias, PSC; Roberto J. Rios

(57) ABSTRACT

The present invention is a method of obtaining and isolating sample spectra from a wide wavelength illumination source without the use of filters. The method obtains the combined sample and illumination spectra of a sample and removes the illumination spectrum from the combined spectrum. This is accomplished by obtaining both the combined sample/illumination spectrum and the illumination spectrum separately at the same time and under the same environmental and instrument conditions. The illumination spectrum is then subtracted, wavelength by wavelength from the combined sample/illumination spectrum, leaving the pure sample spectrum which may a single spectrum or combination of two or more spectra from different types and/or compounds in the sample.

6 Claims, 6 Drawing Sheets a) First Order Spectra of empty chambers b) Second Order Spectrum of empty chambers c) Zero Order Spectrum of empty chambers (sample spectrum adjusted)

METHOD TO REMOVE THE SPECTRAL COMPONENTS OF ILLUMINATION ENERGY FROM A SAMPLE SPECTRUM WITHOUT THE USE OF OPTICAL BARRIER FILTERS, AND APPARATUS FOR THE SAME

TECHNICAL FIELD

The invention relates to a method of obtaining combined sample spectra across wide energy ranges and more particularly to a method of obtaining combined sample spectra across wide energy ranges by eliminating the illumination component without the use of filters.

BACKGROUND OF THE INVENTION

Spectroscopy is the process of separating energies from samples that characterize said samples. In most cases, other than samples that have naturally emitting energies, such as radioactivity and chemi-illuminsance, it is necessary to irradiate the sample with some form of energy that interacts with the sample to cause it to absorb or emit energies that can be detected in the form of a spectrum. Transmission, Reflection and Absorption spectroscopy are the simplest examples of this interaction between the irradiation energy and the resulting energy spectrum from the sample. In the case of Transmission spectroscopy, only those energies that pass through the sample are detectable in a spectrum. With Absorption spectroscopy, it is the absorbed energies that are detectable in the spectrum. In Reflectance spectroscopy, the detectable energies are those that are reflected from a surface while all others are absorbed.

Fluorescence and Raman spectroscopy are more complex techniques since the irradiating energy interacts with the molecular structure exciting the electrons in such a way that the sample emits energies different and non-complimentary from the irradiating source. This kind of description can even be applied to Nuclear Magnetic Resonance spectroscopy where the radiating energy is a spectrum of different magnetic field strengths and the sample spectrum is the result of the spectrum of the resonating atoms of the sample.

In all spectroscopy in which the sample is not naturally emitting energy, the illuminating energy is to some degree, carried along into the resulting spectrum of the sample. For example, in Absorption spectroscopy, especially in the case of infrared spectroscopy, the baseline of the resulting spectra is the illuminating infrared energy where the molecular structure of the sample absorbs the illuminating at specific wavelengths to provide the characteristic absorption spectrum of the sample. In the case of Reflectance spectroscopy, the reflected spectrum of energies from the surface of the sample is superimposed onto the illumination energies.

Where there is a shift in emission energies from the illumination energies, as with Fluorescence and Raman spectroscopy, narrow wavelength energies, provided by lasers, band pass filters and/or notch filters, are used in an attempt to eliminate the illumination energies. This is done, since in many cases, the energy shift is small and the emission energy may be completely masked by the overlap and strength of the illumination energy. In these cases, knowledge of the spectral characteristics of the sample is required, as well as a very specific instrument setup in order to isolate and optimize the emission energies of the sample from the illumination energies.

As can be appreciated, illuminating energy is the key component in obtaining most absorption and emission spectra since either the illumination is absorbed, or it excites the electrons in the sample to a different energy state and when they fall back to their normal state, energy is emitted. However, both absorption and emission of energy characteristics of the illumination may be present in the resulting sample spectra. For example there are strong peaks in illumination spectra when produced from, for example, mercury arc and xenon arc sources. In most synthetic, as well as natural illumination sources, there are absorption bands that are characteristic of the elements producing the illumination, such as from halogen lamps and sunlight or starlight. These extra spectral contributions from the illumination can interfere with the identification of the spectral components from the sample. Usually, filters are used to remove these artifacts. However, the use of filters may also limit the response of the sample and its spectral components. Pure sample spectra would result if the illumination component could be eliminated without the use of filters.

Most samples have a multitude of spectral parameters that characterize and identify them and their composition. However, each form of spectroscopy requires a different instrument that processes the illumination and emission energies in different specific ways to optimize the signal to noise ratio of the sample for that specific form of spectroscopy. It would be convenient, efficient, and more informative, if there were a way to obtain spectral data from a single instrument that presents a single spectrum that represented the combine spectroscopes.

SUMMARY OF THE INVENTION

The present invention is directed to a method of obtaining and isolating individual emission spectra from a wide wavelength excitation source without the use of filters. The key to this method is obtaining the wide combined excitation and emission spectrum of a sample and removing the excitation spectrum from the combined spectrum. This is accomplished by obtaining both the combined excitation/emission spectrum and the excitation spectrum separately at the same time and under the same environmental and instrument conditions. The excitation spectrum is then subtracted, wavelength by wavelength from the combined excitation/emission spectrum, leaving the pure emission spectrum which may a single emission spectra or combination of two or more spectra from different compounds in the sample. In the case of combined emission spectra, the individual emission spectra are obtained by deconvoluting the emission spectrum using models of known emission spectra.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

The present invention describes a novel methodology named by the inventors "Combined Spectroscopy", which is based on the complete removal of the illumination component from spectral data of a sample to reveal hidden spectral information about the sample not previously available from a single procedure and/or using a single apparatus.

With most forms of spectroscopy, illumination (irradiation) energy is directed against a sample. The sample will interact with that illumination and respond by either transmitting, absorbing, reflecting or shifting emitted wavelength. However, since the illumination energy is not consumed by the sample, spectral data from the illumination is present in the resulting sample spectrum. The presence of this data in the sample spectrum can mask spectroscopic components of the sample. By eliminating the illumination energy data from the spectral data of the sample, the resulting sample spectrum can reveal multiple spectral parameters that were hidden in the presence of the illumination data.

In accordance with the inventor's novel methodology the following novel concepts and terms will be defined and use throughout the specification. Combined Spectroscopy is the novel method of obtaining a Combined Spectrum by means of a filter-less Spectroscopy technique that eliminates the illumination source component from the final spectrum. Combined Spectrum is the spectrum that contains components from multiple spectral sources without the illuminating source data. Zero Order Spectrum is the spectrum resulting from equalizing the spectra from a reference chamber and a sample chamber across the wavelength range. First Order Spectra is the spectra from the reference chamber and sample-containing chamber after the Zero Order Spectrum has been established. Finally, Second Order Spectrum is the resulting spectrum, (i.e., the Combined Spectrum), after the illumination spectrum has been eliminated from the sample spectrum by subtracting the First Order Spectrum of the illumination from the First Order Spectrum of the sample.

Figure 1:
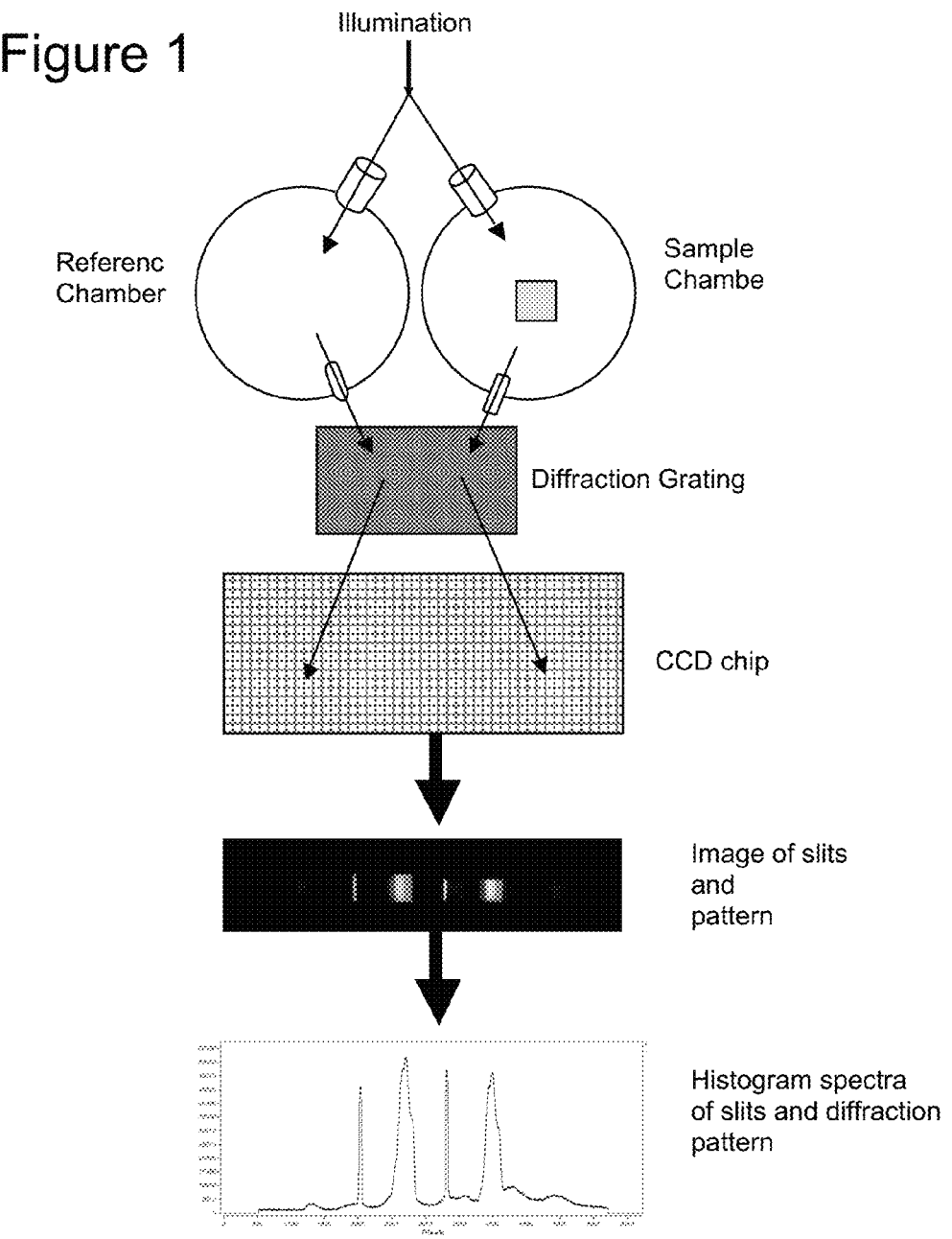
FIG. 1 illustrates the major components of the Combined Spectrometer in operation, according to the present invention.

The methodology of the present invention is carried out by using an apparatus named by the inventors as a "Combined Spectrometer". In general, the Combined Spectrometer consists of two separate chambers (reference and sample) that have the same size, shape and reflectivity properties as illustrated in FIG. 1. Each chamber has a inlet port to introduce illumination into the chambers that may have a wide or narrow wavelength range of electromagnetic energy (e.g., UV to IR). This energy will be reflected by the surface of the chambers and exit through a outlet port. In the preferred embodiment, the outlet port is a slit with controlable geometry in each chamber. The illumination from the slits are directed through a prism or diffraction grating that will defract the electromagnetic energy into their respective spectral components. As shown in FIG. 1, the two sets of spectral data are then directed onto separate areas of a charge coupled devise (CCD) that has an appropriate pixel resolution so that a computer can then read and manipulate each of the data sets to form a spectrum of the illumination and a spectrum that contains sample and illumination information, respectively. Data from these pixels are then calibrated and manipulated by computer software to produce the Combined Spectrum of the sample.

As part of the procedure to acquire a Combined Spectrum according to the present invention, a Zero Order Spectrum must be obtained prior to introducing the sample into the sample chamber. This spectrum represents that the chambers of the spectrometer have been equalized or normalized and that the intensity readings in the sample chamber across the whole wavelength range of interest are zero. This is accomplished by introducing the illumination into both chambers of the instrument without the sample present. The slits geometries and the illumination power settings are mechanically adjusted such that the resulting illumination spectra, First Order Spectra, from the two chambers are equal across the wavelength range.

In practice, this can not be accomplished perfectly using only mechanical adjustments. However, zero intensity values across the wavelength range can be obtained from the Zero Order Spectra by calibrating or adjusting both spectra in terms of wavelengths and then subtracting the illumination spectrum from the spectrum derived from the sample chamber without the presence of the sample. The resulting intensity differences resulting from the subtraction between the two spectra are determined wavelength by wavelength and the intensities of the sample spectrum are adjusted such that when the illumination spectrum is now subtracted from the sample spectrum, the resulting Zero Order Spectrum has zero intensity values across the wavelength range of the experiment. The sample is then placed into the sample chamber and First Order Spectra are obtained from the chambers under the Zero Order hardware and software conditions. The spectrum from the reference chamber contains data of the illumination alone, whereas the spectrum from the equalized sample chamber contains data from the sample, as well as the illumination.

The Second Order Spectrum is then obtained by subtracting the First Order illumination spectrum from the First Order Sample spectrum, wavelength by wavelength. The resulting Second Order Spectrum is now free of spectral components from the illumination and environmental artifacts effecting the illumination because the procedure to obtain the Zero Order Spectrum equilibrated or compensated for the illumination components and environmental artifacts in both the illumination and sample.

Although the Second Order Spectrum is free of illumination components, it will contain components from a number of spectral sources, including, but not limited to, Transmission, Absorption, Reflection, Fluorescence, Raman scatter, and Complimentary Color Reflection. For wavelengths where there are no spectral components from the sample, the intensity values remain zero in the Second Order Spectrum, as they do in the Zero Order Spectrum.

Applications of Combined Spectroscopy

Combined Spectroscopy can be very useful when first examining samples of unknown composition. The Second Order Spectrum can be produced from illumination sources that cover a wide range of wavelengths including those reflected illumination from artificial and natural sources, e.g., the sun. With a wide wavelength range, the absorption characteristics of the sample are immediately apparent within that range, as well as, indications of fluorescence emission. At this point, fluorescence emission can be confused and hidden within the complementary color component of the Combined Spectrometer. By using a narrow wavelength band of illumination that completely falls within the absorption envelope (excitation spectrum) of the sample, the complementary color component is eliminated because there are no complimentary colors in a narrow illumination band that can be reflected.

Having multiple spectral components, may be considered to be confusing if only specific individual spectral components are desired. To that end, it is possible to isolate them through manipulation of the illumination energy, as discussed in the fluorescence example, or by mathematical modeled deconvolution applications. However, the composite of the multiple spectral sources (absorption, fluorescence, Raman scatter, etc.) in the Combined Spectrum (Second Order) may provide a more definitive identification than a spectrum from a single form of spectroscopy.

Combined Spectroscopy can also be applied in a remote reflective format where the actual sample is outside of the instrument. This is achieved by identifying a surface devoid of the sample that is equivalent to the surface where the sample is located. Then illuminate both surfaces with an illumination source and directing the reflected energy from the reflected energy of the surface devoid of the sample into the reference chamber and the reflected energy from the sample surface into the sample chamber. The data from the two chambers need to be obtained simultaneously. This becomes extremely important when applying Combined Spectroscopy under a reflectivity format where the sample may be a great distance from the spectrometer, such as obtaining a Second Order Spectrum of the Red Tide algae from an airplane or a satillite in space. Artifacts like water vapor, aeresols, thermal density turbulence of the air add significant noise to the signal, but can be eliminated by first obtaining a Zero Order Spectrum, then taking the reflective illumination and sample data, e.g., using the sun as the illumination source and taking the reflected illumination spectrum from on a open part of the ocean, and taking the reflected sample spectrum from a cosal area of water containing the Red Tide algae and then proceeding to obtain the First and Second Order Spectra, as previously described.

Combined Spectroscopy can be applied in a number of fields, especially those that are exploratory where the composition of the sample is unknown. The Combined Spectrum could quickly indicate the preferred type of conventional spectroscopic instrument and its setup parameters such that a more refined qualitative and quantitative analysis could be performed. Such fields would include, but not be limited to geology, forensic analysis, medicine, quality control in manufacturing, astronomy, environmental science, wildlife management. In addition, Combined Spectroscopy data can be used in a scanning mode to create images based on specific spectral parameters. For example, the combined parameters of absorption and fluorescence of Red Tide algae could be used to image the algae blooms along coastal waters from space, or image the particular biological components in tissue such as collagen. More specifically, there are only two possible ways to form an image: either every picture point is formed simultaneously (in parallel) or each is formed sequentially. Historically, these concepts were well known since the mid nineteenth century. All spectral imaging is essentially "analytical" in the sense that one is dealing with a scattering phenomenon, the interaction of particles (waves) with matter and the subsequent registration of the signal, which is solely dependent on the physics of that interaction.

In both simultaneous and sequentially obtained images, quantitative information is retrievable using spectrum imaging; this technique enables the collection and storage of complete spectra at each pixel for either on-line or for post facto analysis. However in the case of parallel techniques the use of localized information acquisition to obtain predetermined statistical precision for quantitative analysis, for example from sub-planetary (e.g. regions on Earth or Mars) or sub-microscopic biological entities, is not possible. Various analytical methods can be applied to a resultant spectral data cube, ranging from simple elemental region-of-interest images, to spectral summation of the pixel elemental weight percent, to true chemical phase images. While spectrum imaging is an important tool in image analysis, until recently implementation still lacked true integration with scan generation and the collection of other signals of interest, such as fluorescence or x-ray images. A recent method, Event-Streamed Spectrum Imaging (ESSI), disclosed in U.S. Pat. No. 7,858,935 to Davilla et all. (incorporated herein by reference in its entirety) has been developed that overcomes these and other limitations.

The net results between conventional methods of spectrum imaging and the ESSI method, while being similar for specific wavelength/energy mapping alone, can be far more comprehensive for scanning techniques such as ESSI in that all parameters of interest (for example illumination, operating conditions, drift corrections, regions of acquisition, temperature, technical equipment parameters. weather data etc.) can be included at every pixel and either imaged and manipulated in real time or stored for later display as single or multiple frames (movies) off-line. Of particular importance is the use of dynamic dwell modulation or Programmed Beam Acquisition (PBA) that enables the exciting radiation to dwell only for sufficient times per pixel in regions of the specimen necessary to acquire a predetermined statistical precision (e.g. ±2 standard deviations). In both methods the use of scatterplots (2-D histograms) can be indispensable in locating regions requiring further analysis. Since every pixel in an illumination image is indexed to the same pixel in elemental or chemical images for example, masks can be created that will identify regions of the cell to which further examination can be directed. The use of PBA and scatterplot protocols together with ancillary analytical techniques such as multivariate statistical analysis, principal component and/or maximum pixel analyses can be very useful in providing more accurate and rapid identification and quantitative data than parallel or single chemical mapping alone. The method of the present invention can be used and/or integrated as part of these techniques to provide better empirical and/or analytical data.

According to a preferred embodiment of the invention, a Combined Spectrometer is built as illustrated in FIG. 1 that consists of two equal chambers that are the same size and shape (for example, spherical or parabolic) and coated with a highly uniform wide wavelength reflective material, such as but not limited to titanium oxide. Each chamber will have a port through which illumination energy can be introduced via a lens and/or fiber optic. Each chamber will be fitted with an adjustable slit mechanism (X-axis to adjust resolution and Y-axis to increase intensity) to equalize or normalize the illumination energy in the two chambers. The sample chamber will contain a removable sample holder such that samples could be placed in the chamber, or the instrument could be operated in a reflective format where the sample holder is removed from the chamber and illumination energy reflected from remote surfaces that do and do not contain sample is introduced into the respective chambers through their illumination ports. The instrument will contain a diffraction grating of sufficient resolution that matches or is greater than the resolution of the CCD detection chip (e.g., 2,400 lines/mm). Data from the two chambers will be stored and processed in a correlated manner such that the illumination only data from the one chamber and the sample containing illumination data from the second chamber are paired together across the time frame of the exposure.

The utility and effectiveness of the method of the present invention was confirmed using a Combined Spectrometer prototype constructed from a white box that was divided by into two chambers, each of which contained a slit that directed the reference and sample energies through a 100 line/mm diffraction grating which in turn projected the image of the slit (zero diffraction) along with the diffraction spectrum from the grating into a Canon T2i digital camera affixed with a 50 mm lens. Photographs were taken at 1/100 sec exposures at an ASA 1600. The image of the slit and spectrum was converted into a raw graphic spectrum as a function of pixel position on the camera by software (Rspec by Field Test Systems).

Figure 2:
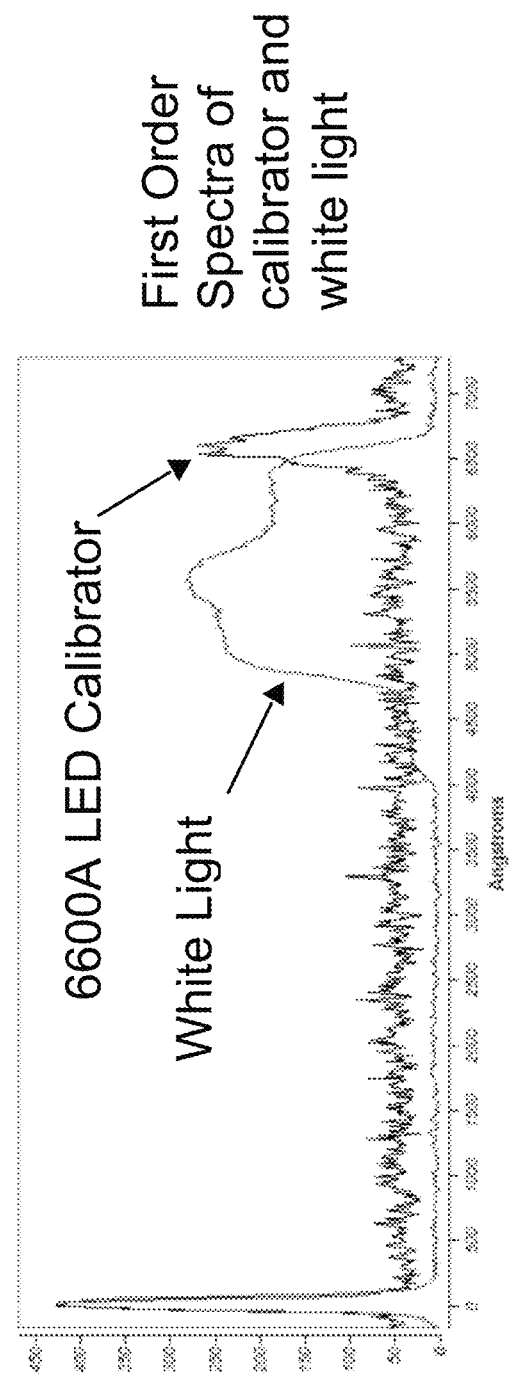
FIG. 2 shows spectrum of the red 6600A LED used in converting and calibrating pixels into Angstroms along with a sample to be calibrated, according to the present invention.

Raw graphic spectra were calibrated and converted into wavelengths by obtaining a diffraction spectrum of a red LED (6600A) illumination. The pixel separation between the zero diffraction pixel of the slit and the 6600A peak pixel was used to calibrate the spectra of the reference and sample energies as shown in FIG. 2.

Figure 3:
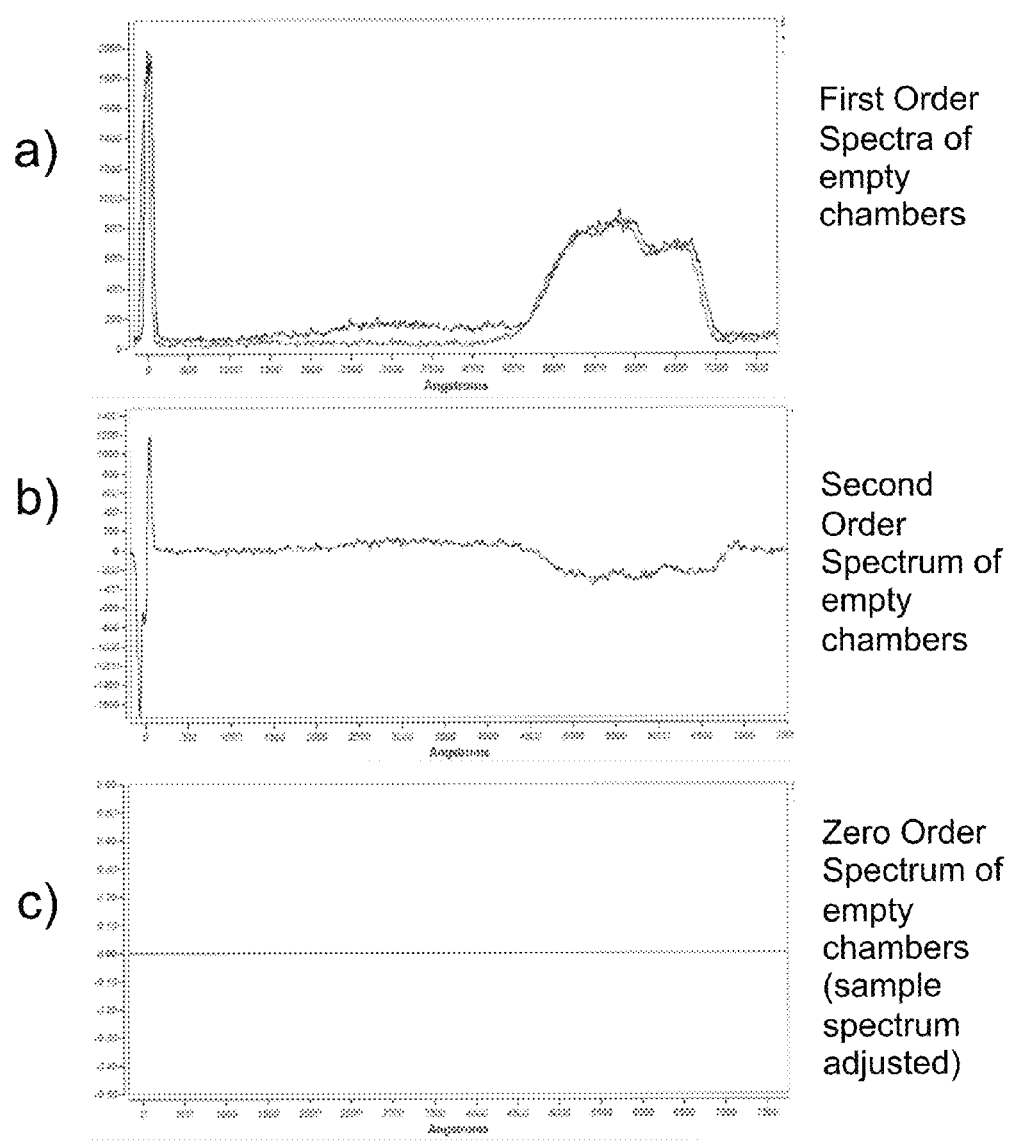
FIG. 3 shows spectra used in the method to obtaining a Zero Order Spectrum, according to the present invention.

The Zero Order spectrum was obtained by illuminating both empty chambers of the prototype Combined Spectrometer with a white halogen light and taking a picture of the slit and diffraction spectra generated from the two chambers. These diffraction spectra were converted to graphic spectra and calibrated against the Red LED as shown in plot (a) of FIG. 3. The First Order Spectrum of the reference chamber was subtracted, wavelength-by-wavelength from the First Order Spectrum from the empty sample chamber as shown in plot (b) of FIG. 3. Although most of the spectral illumination data was eliminated, intensity values were still present in the preliminary Zero Order Spectrum due to differences in size, reflectivity, illumination positioning, and other sources of artifacts. These intensities were corrected by determining their magnitude between the two chambers at each wavelength with respect to the illumination spectrum and then applying them to the sample chamber spectrum such that the Zero Order Spectrum indicated zero intensity across the wavelength range of interest as shown in plot (c) of FIG. 3.

Figure 4:
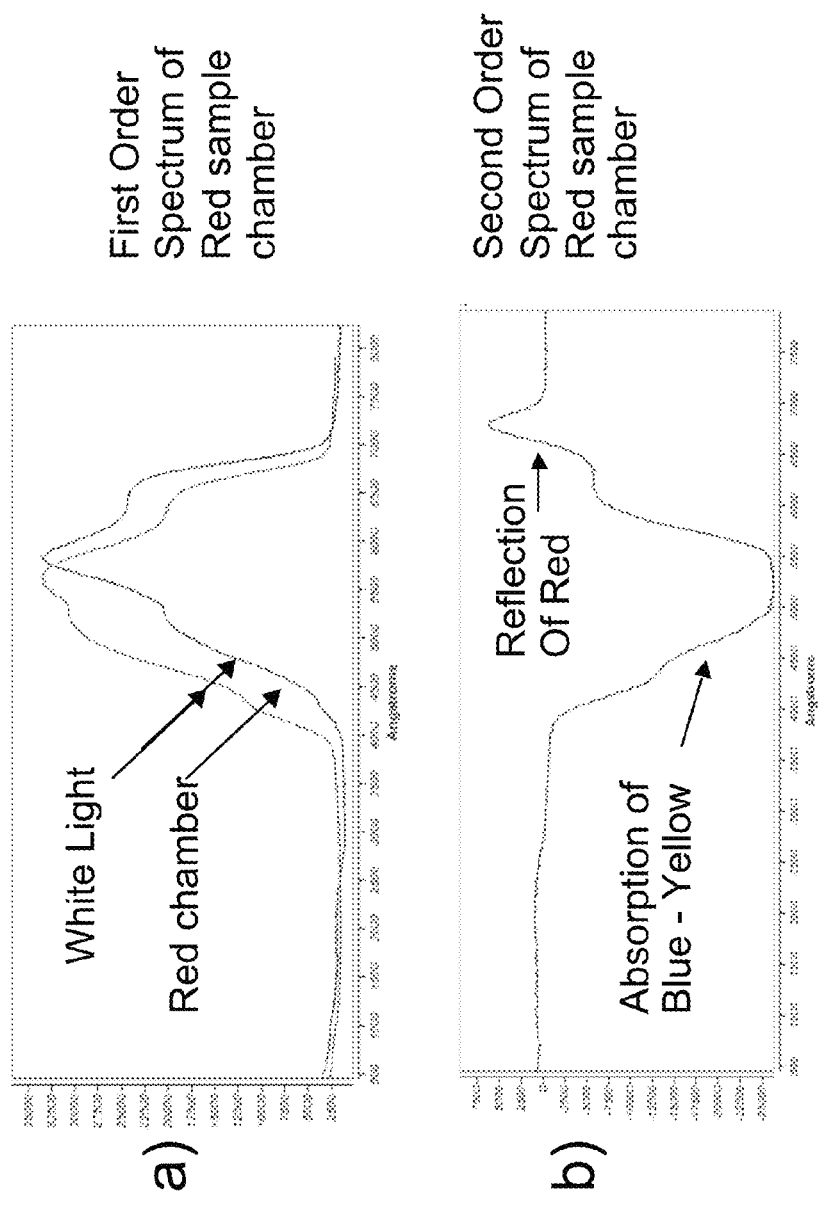
FIG. 4 shows spectra illustrating the complimentary color contribution, according to the present invention.

The contribution of complimentary colors according to the method of the present invention, was demonstrated by placing a piece of red cardboard into the sample chamber and illuminating both chambers with white halogen light. First Order Spectra were obtained from both chambers as previously explained. Note that only about 30% of the reflecting area was covered by the red cardboard. The resulting First Order Spectra appeared shifted from each other when superimposed in a graph as shown in plot (a) of FIG. 4. The Second Order Spectrum revealed that the red cardboard reflected data in the red region (6000-7000 A) and absorbed the complimentary blue to yellow colors (4000-6000 A) as shown in plot (b) of FIG. 4.

Figure 5:
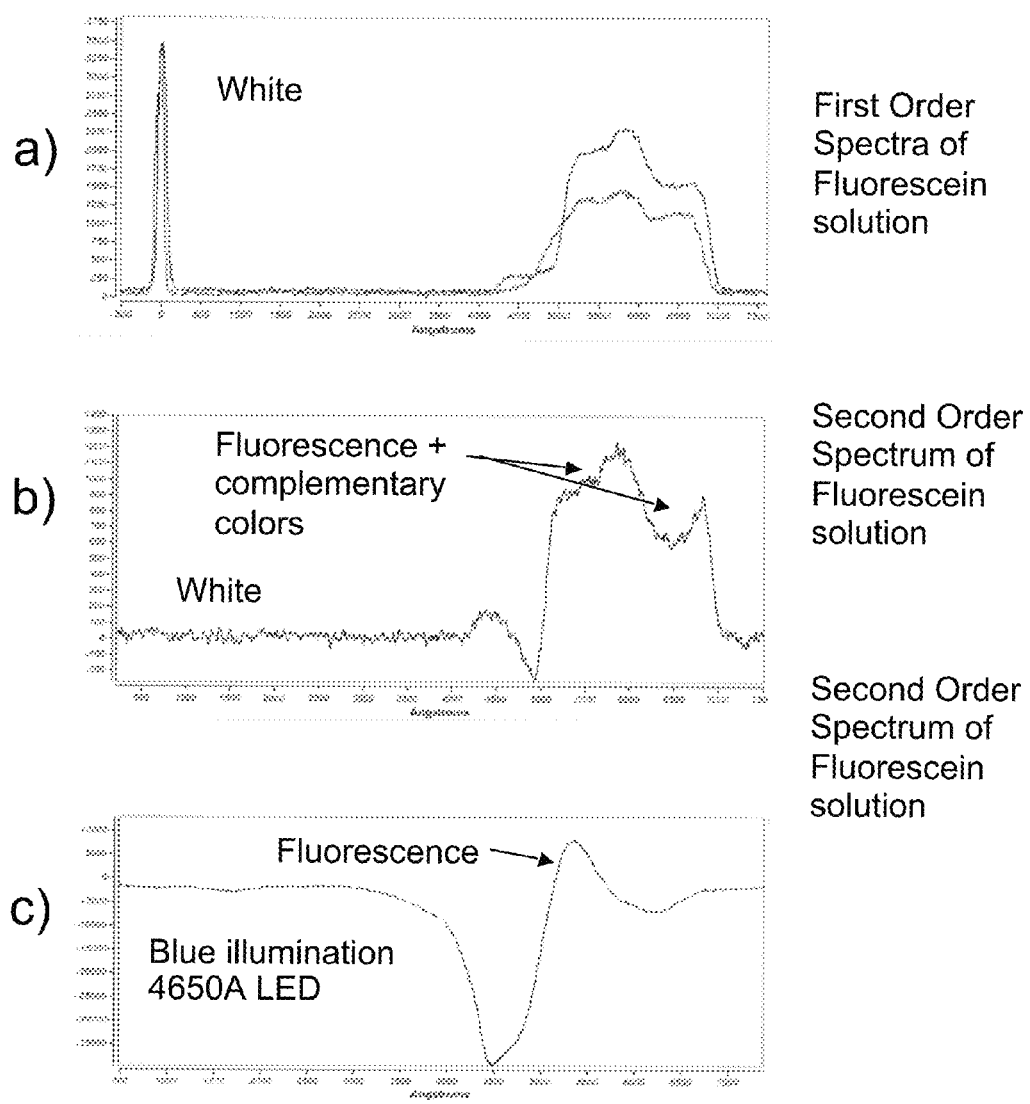
FIG. 5 shows Fluorescence Emission Spectra in the Combined Spectrum, according to the present invention.

The Combined Spectrometer prototype was used to demonstrate that fluorescence spectra can be obtained using Combined Spectroscopy, according to the present invention. A curvet of fluorescein solution (pH>7) was placed in the sample chamber and the chambers were illuminated with white halogen light. First Order spectra from the illumination and sample chambers were obtain by the previously described method as shown in plot (a) of FIG. 5. The Second Order Spectrum shows distinct absorption across the excitation range of fluorescein (4000-(4930 peak)-5500 A), as well as wide emission range (4800-(5200 peak)-6500 A) as shown in plot (b) of FIG. 5. However, complimentary colors may also be present since the solution appears green in white light. However, when the First Order Spectra from the two chambers are obtained using a narrower blue illumination (4000-(4650 peak)-6000 A) wavelength, then there are no reflected complimentary colors to confuse the situation and thus the emission of the fluorescein sample is revealed as shown in plot (c) of FIG. 5.

Figure 6:
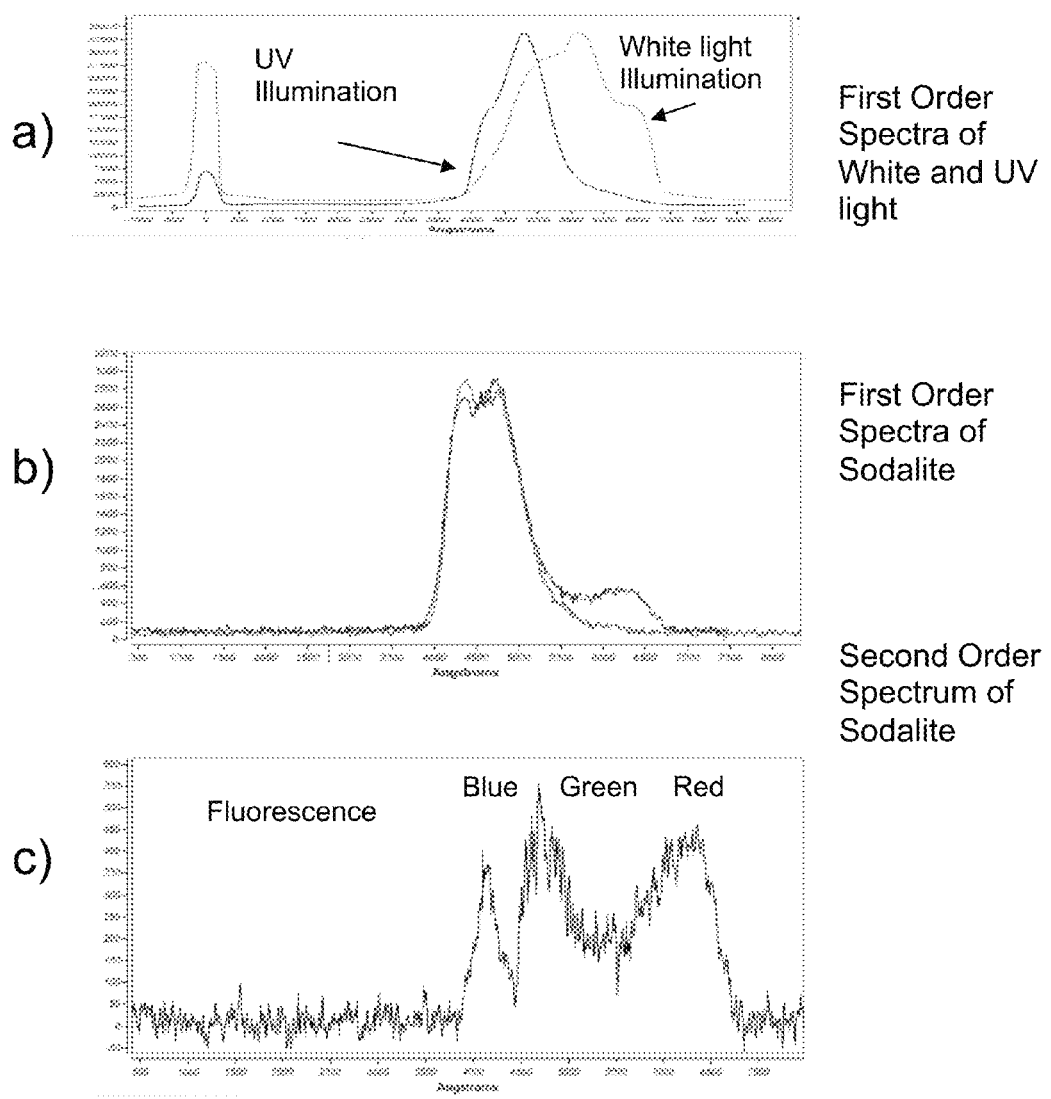
FIG. 6 shows spectra of Fluorescence from a geological sample (Sodalite), according to the present invention.

A fluorescence spectrum from a geological sample was demonstrated by placing a Sodalite rock in the Combined Spectrometer prototype, according to the present invention. The difference between illumination from white light and UV (3660 A) light is illustrated in plot (a) of FIG. 6. A sample of Sodalite was placed in the sample chamber and both chambers were illuminated with a UV (3660 A) lamp. First Order Spectra from the two chambers was obtained as previously explained as shown in plot (b) of FIG. 6. The Second Order Spectrum was obtained by subtracting the illumination First Order Spectrum from the sample First Order Spectrum as shown in plot (c) of FIG. 6. Note that the absorption peak of the 3660 A illumination was not present in the Illumination First Order Spectrum due to the camera being insensitive to wavelengths below 4000 A. The Second Order Spectrum however reveals that blue, green and red fluorescence is present in the emission spectrum.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. A method to remove the spectral components of illumination energy from a sample spectrum without the use of optical barrier filters, the method comprising:

obtaining from a reference chamber and from an empty sample chamber a first set of illumination spectra when illumination energy is provided simultaneously to said reference and empty sample chambers;

determining the intensity differences between the illumination spectrum from said reference chamber and the illumination spectrum from said empty sample chamber at each wavelength across the illumination wavelength range;

obtaining from said reference chamber and sample chamber a second set of spectra wherein the spectrum from the reference chamber contains only illumination spectral components and the spectrum from said sample chamber contains both illumination and sample spectral components when illumination energy is provided simultaneously to said reference and sample chambers;

adjusting the intensities of the illumination spectrum from said reference chamber of the second set of spectra across the wavelength range of the illumination by subtracting or adding the previously determined intensity difference at each corresponding wavelength to the intensities of said illumination spectrum wavelength from said reference chamber of the second set of spectra to make the illumination intensities from said chambers equal across the illumination wavelength range; and subtracting the said adjusted illumination spectrum of the said second set of spectra from the spectrum from said sample chamber of the second set of spectra that contains both illumination and sample components, effectively removing the spectral component of illumination energy from a sample spectrum.

2. The method of claim 1, wherein said sample is located inside said sample chamber.

3. The method of claim 1, wherein said sample is located outside said sample chamber and reflected energy from the sample surface is directed into the sample chamber.

4. A method to remove the spectral components of illumination energy from a sample spectrum without the use of optical barrier filters, the method comprising:

directing energy outputted from a reference chamber and a sample chamber to a diffraction grating that diffracts the received energy onto a CCD chip to generate a first set of illumination spectra when illumination energy is simultaneously provided to said reference chamber and to said sample chamber while said sample chamber is empty;

determining from said first set of illumination spectra the intensity differences between the illumination spectrum from said reference chamber and the illumination spectrum from said empty sample chamber at each wavelength across the illumination wavelength range;

directing energy outputted from said reference chamber and said sample chamber to said diffraction grating that diffracts the received energy onto a CCD chip to generate a second set of illumination spectra when illumination energy is simultaneously provided to said reference chamber and to said sample chamber, the spectrum from the reference chamber contains only illumination spectral components and the spectrum from said sample chamber contains both illumination and sample spectral components;

adjusting the intensities of the illumination spectrum from said reference chamber of the second set of spectra across the wavelength range of the illumination by subtracting or adding the previously determined intensity difference at each corresponding wavelength to the intensities of said illumination spectrum wavelength from said reference chamber of the second set of spectra to make the illumination intensities from said chambers equal across the illumination wavelength range; and subtracting said adjusted illumination spectrum of said second set of spectra from the spectrum from said sample chamber of the second set of spectra that contains both illumination and sample components, effectively removing the spectral component of illumination energy from a sample spectrum.

5. The method of claim 4, wherein said sample is located inside said sample chamber.

6. The method of claim 4, wherein said sample is located outside said sample chamber and reflected energy from the sample surface into directed into the sample chamber.

* * * * *